(12) United States Patent
Ferguson et al.

(10) Patent No.: US 11,751,865 B2
(45) Date of Patent: *Sep. 12, 2023

(54) METHOD OF PERFORMING A TENDON REPLACEMENT

(71) Applicant: RIVERPOINT MEDICAL, LLC, Portland, OR (US)

(72) Inventors: Patrick Joseph Ferguson, Portland, OR (US); Patrick Edward Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 389 days.

This patent is subject to a terminal disclaimer.

(21) Appl. No.: 17/151,433

(22) Filed: Jan. 18, 2021

(65) Prior Publication Data

US 2021/0137515 A1 May 13, 2021

Related U.S. Application Data

(63) Continuation of application No. 16/210,376, filed on Dec. 5, 2018, now Pat. No. 10,893,860, which is a
(Continued)

(51) Int. Cl.
*A61B 17/04* (2006.01)
*A61F 2/08* (2006.01)
(Continued)

(52) U.S. Cl.
CPC .......... *A61B 17/0401* (2013.01); *A61B 17/04* (2013.01); *A61B 17/06166* (2013.01);
(Continued)

(58) Field of Classification Search
CPC . A61B 17/04; A61B 17/0401; A61B 17/0485; A61B 17/06166;
(Continued)

(56) References Cited

U.S. PATENT DOCUMENTS 5,306,301 A 4/1994 Graf et al.
6,517,578 B2 2/2003 Hein
(Continued)

OTHER PUBLICATIONS

Boyle, M.J. et al., ACL TightRope Scientific Update, Arthrex, Inc., LA1-00021-EN_B, pp. 1-2, 2016.
(Continued)

*Primary Examiner* — Robert A Lynch
(74) *Attorney, Agent, or Firm* — BrainSpark Associates, LLC (57) ABSTRACT

A suture assembly, including a button having two apertures and a suture defining a lumen and forming a double loop, formed by a double trap formed in the suture, opposed to the button, and in which a first portion of the suture is threaded through the lumen of the double trap and a second portion of the suture is also threaded through the lumen of the double trap, so that two portions of suture are positioned together in the double trap. The first portion of the suture, after emerging from the double trap, is threaded through the lumen again, thereby forming a second trap, increasing resistance of the double loop to expansion, the double loop being threaded through the apertures of the button, the suture having two suture ends that are threaded through the button apertures and accessible on a side of the button opposed to the double loop.

15 Claims, 8 Drawing Sheets

Related U.S. Application Data continuation of application No. 15/694,338, filed on Sep. 1, 2017, now Pat. No. 10,194,900, which is a continuation of application No. PCT/US2017/026353, filed on Apr. 6, 2017.

(60) Provisional application No. 62/319,115, filed on Apr. 6, 2016.

(51) Int. Cl.
*A61B 17/06* (2006.01)
*A61B 17/00* (2006.01)

(52) U.S. Cl.
CPC .............. *A61F 2/08* (2013.01); *A61F 2/0811* (2013.01); *A61B 17/0485* (2013.01); *A61B 2017/00526* (2013.01); *A61B 2017/0404* (2013.01); *A61B 2017/0459* (2013.01); *A61B 2017/0477* (2013.01); *A61B 2017/061* (2013.01); *A61B 2017/06185* (2013.01); *A61F 2002/0817* (2013.01); *A61F 2002/0852* (2013.01); *A61F 2002/0882* (2013.01); *A61F 2230/0004* (2013.01); *A61F 2230/0019* (2013.01); *A61F 2250/0007* (2013.01)

(58) Field of Classification Search
CPC .. A61B 2017/00526; A61B 2017/0404; A61B 2017/0477; A61B 2017/0459; A61B 2017/061; A61B 2017/06185; A61F 2/08; A61F 2/0811; A61F 2002/0817; A61F 2002/0852; A61F 2002/0882; A61F 2230/0004; A61F 2230/0019; A61F 2250/0007

See application file for complete search history.

(56) References Cited

U.S. PATENT DOCUMENTS

| | | | |
|---|---|---|---|
| 8,088,130 B2 | 1/2012 | Kaiser et al. | |
| 8,118,836 B2 | 2/2012 | Denham et al. | |
| 8,460,379 B2 | 6/2013 | Albertorio et al. | |
| 9,204,960 B2 | 12/2015 | Albertorio et al. | |
| 9,216,078 B2 | 12/2015 | Conner et al. | |
| 9,333,069 B2 | 5/2016 | Denham | |
| 9,963,319 B2 | 5/2018 | Ferguson | |
| 10,194,900 B2 * | 2/2019 | Ferguson | A61B 17/06166 |
| 10,893,860 B2 * | 1/2021 | Ferguson | A61F 2/08 |
| 2007/0233151 A1 | 10/2007 | Chudik | |
| 2008/0312689 A1 | 12/2008 | Denham et al. | |
| 2009/0312776 A1 | 12/2009 | Kaiser et al. | |
| 2009/0318961 A1 | 12/2009 | Stone et al. | |
| 2010/0268273 A1 | 10/2010 | Albertorio et al. | |
| 2013/0317544 A1 | 11/2013 | Ferguson et al. | |
| 2015/0157449 A1 | 6/2015 | Gustafson | |
| 2015/0173739 A1 | 6/2015 | Rodriguez et al. | |
| 2016/0128684 A1 | 5/2016 | Stone et al. | |
| 2017/0360437 A1 | 12/2017 | Ferguson et al. | |
| 2018/0008257 A1 | 1/2018 | Ferguson et al. | |

OTHER PUBLICATIONS

Watson, John, "Endobutton CL Ultra fixed-length cortical suspension device vs. adjustable-loop fixation designs: Review of mechanical data". Bone & Joint Science, vol. 4, No. 4, pp. 1-9, Oct. 2004.

Patent Cooperation Treaty (PCT), International Searching Authority, Application No. PCT/US17/26353, International Search Report and Written Opinion, dated Aug. 1, 2017.

Barrow, AE et al., Femoral Suspension Devices for Anterior cruciate ligament reconstruction: do adjustable loops lengthen?, Am J Sports Med. Feb. 2014; 42(2):343-9. doi: 10.1177/0363546513507769. Epub Oct. 24, 2013.

"Advanced ACL/PCL Graft Fixation Options . . . Simplified", TightRope Implant, Arthrex, Inc., LB1-0179-EN-B, pp. 1-12, 2016.

McCarty, Eric, M.D., "ACL Reconstruction" Biomet Sports Medicine, Mar. 2009.

* cited by examiner

METHOD OF PERFORMING A TENDON REPLACEMENT

RELATED APPLICATIONS

This application is a continuation of U.S. patent application Ser. No. 16/210,376, filed Dec. 5, 2018, issuing as U.S. Pat. No. 10,893,860 on Jan. 19, 2021, which itself is a continuation of U.S. patent application Ser. No. 15/694,338, filed on Sep. 1, 2017, now U.S. Pat. No. 9,963,319, issued May 8, 2018, which itself is a continuation of International Application number PCT/US17/26353, filed on Apr. 6, 2017, which claims the benefit of priority to U.S. Provisional Application No. 62/319,115, filed Apr. 6, 2016, all of which are incorporated herein by reference as if fully set forth herein.

TECHNICAL FIELD

The present invention is in the field of variable-width suture loop-button constructs for ligament implantation surgery, and surgery performed using the same.

BACKGROUND ART

Continuous loop suture and button assemblies are commonly used during orthopedic surgery for bone-tendon-bone, single-bundle soft tissue, and double bundle soft tissue fixation, such as during cruciate reconstruction. For example, during anterior cruciate ligament (ACL) reconstruction, a bone-tendon-bone graft is commonly positioned within both the femur and tibia bones. These grafts are often secured to a continuous loop/button assembly, which are in turn anchored to a bone. One example of a loop/button assembly is disclosed in U.S. Pat. No. 6,533,802 to Bojarski et al. ("Bojarksi"). Bojarski references a few different general methods of attaching a button to a continuous loop: (a) start with a closed loop suture and then capture the button by threading loop sections through openings in the button or wrapping the loop sections around channels/arms of the button (e.g., Bojarksi FIG. 12), (b) start with a thread having a leading end and utilize an automated winding machine to continuously wrap the leading end through apertures in the button to form a closed loop, such as disclosed in WO99/47079 to Bryant ("Bryant"), or (c) provide a suture with two open ends, thread and/or wrap the suture to an anchor button and then tie the open ends together, such as disclosed in U.S. Pat. No. 5,769,894 to Ferragamo ("Ferragamo"). The above described methods, of making continuous loop and button assemblies, result in products that are susceptible to breaking over time due to mechanical stress.

Additionally, U.S. Pat. No. 9,357,990 describes an assembly having a fixed sized loop attached to a button. This has provided a helpful advance in the art.

U.S. Pat. No. 6,517,578 discloses a device similar to those described in the references discussed above, except for that the suture loop that is threaded through the buttonholes has a variable size. To achieve this result, a double trap is used with two suture lengths crossing each other inside a lumen in another length of the same suture. This adjustability permits the surgeon using the device to adjust it prior to use, and also to adjust the loop size during surgery. There is an advantage in not having to keep many different sizes of suture loop-button constructs on hand for surgeries on patients with differing bone thicknesses. Unfortunately, during use, the loop tends to expand, due to slippage in the double trap, leading to problems with the ligament implantation. Efforts to create a suture having less slippage by expanding the length of the double trap have met with issues in the construction of the construct.

SUMMARY

A suture assembly, including a button having two apertures and a suture defining a lumen and forming a double loop, formed by a double trap formed in a double trap portion of the suture, opposed to the button, and in which a first portion of the suture is threaded through the lumen of the double trap portion and a second portion of the suture is also threaded through the lumen of the double trap portion, so that two portions of suture are positioned together in the double trap. Further wherein the first portion of the suture, after emerging from the double trap, is threaded through the lumen again, thereby forming a second trap, additional to the double trap, and thereby increasing resistance of the double loop to expansion, after it has been tightened, the double loop being threaded through the apertures of the button, the suture having two suture ends that are threaded through the button apertures and accessible on a side of the button opposed to the double loop.

A method of performing a tendon replacement, of a tendon connecting a first bone and a second bone, in an animal body that utilizes a construct that includes a button having two apertures and a suture defining a lumen and forming a double loop, formed by a double trap having a first end and a second end, formed in a double trap portion of the suture, opposed to the button. A first portion of the suture is threaded through the lumen of the double trap portion and a second portion of the suture is also threaded through the lumen of the double trap portion, so that two portions of suture are positioned together in the double trap and further wherein the first portion of the suture, after emerging from the second end of the double trap, is threaded through the lumen again, thereby increasing resistance of the double loop to expansion, after it has been tightened. Further, the double loop being threaded through the apertures of the button, the suture having two suture ends that are threaded through the button apertures and accessible on a side of the button opposed to the double loop. The method starts by drilling a drill hole sequentially through the two bones. a suture assembly. Lengths of tendon tissue are draped over the double loop and passing the button through the drill hole through the first bone and the second bone and orienting the button to sit on a surface of the second bone with the suture ends extending outwardly through the apertures of the button. Finally, the suture ends are pulled to constrict the double loop.

DETAILED DESCRIPTION

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
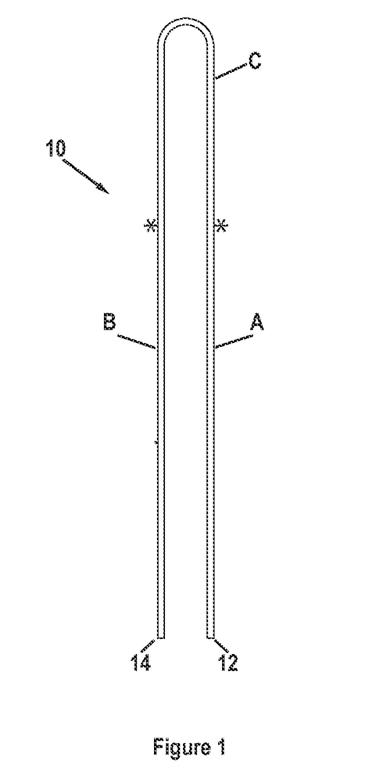
FIG. 1 is an illustration of a suture showing the definition of three regions.
Figure 2:
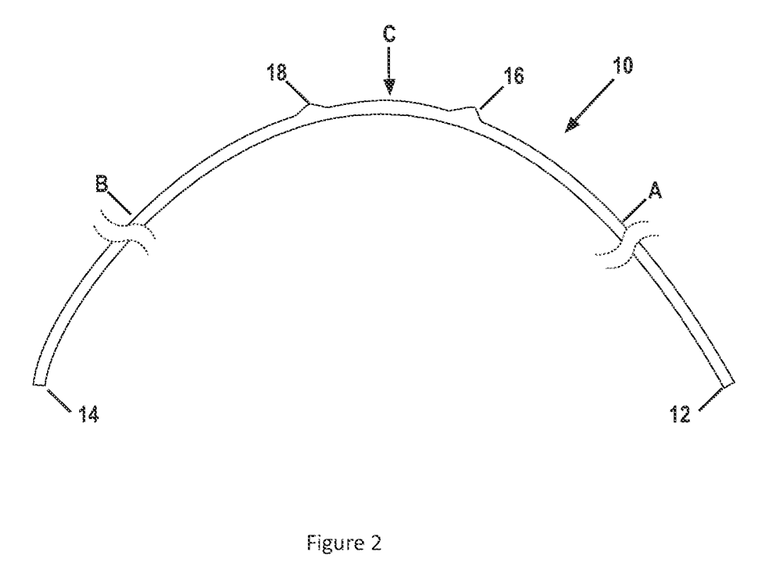
FIG. 2 is an illustration of the suture of FIG. 1, with two places fluffed to facilitate introduction of a suture portion into a lumen defined interior to the suture.

FIG. 1 shows a length of fiber or suture 10, bent in a U-shape and having a first tail 12 and an opposed second tail 14. Also, three thirds of the suture 10 are indicated, a first third A, an opposing third B, and a central third C. In a preferred embodiment, suture 10 is a braid that defines an inner lumen. As shown in FIG. 2, the suture 10 is preferably fluffed at the entry point 16 and exit point 18 points to make it easier for a lacing tool 22 (FIG. 3) to be inserted through the trap section 20. One end of the lacing tool 22 can include a handle to allow a user to position, guide, push, and pull the tool. The lacing tool 22 also includes a main body that is preferably substantially linear and having a diameter, or cross-section, small enough to thread through the suture 10. The end of the lacing tool 22 opposite of the handle can include a hinged barb 24 to allow for coupling to the suture 10. The hinge allows the barb 24 to have a lower profile when traversing through the inside of suture 10 while minimizing the chance of snags. Other means for coupling to the suture 10 are readily contemplated and can nonexclusively include one or more barbs (hinged or unhinged) hooks, clamps (such that can be opened and closed by the handle) and the like, for example. Said means for coupling preferably should not prevent or hinder the lacing tool 22 from being pushed into or pulled out of the inside of the suture 10. In a preferred embodiment fiber or suture 10 is made of ultra-high molecular weight polyethylene (UHMWPE).

Figure 3:
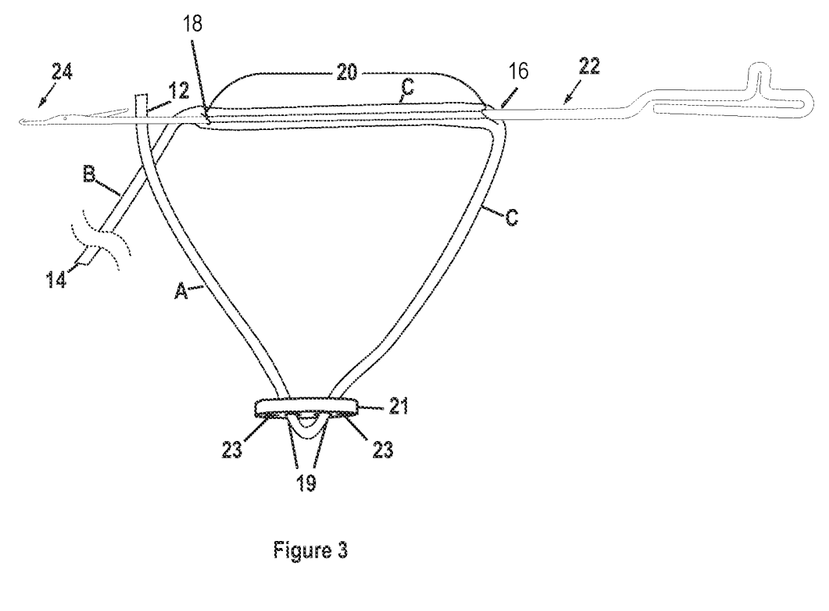
FIG. 3 is an illustration of the suture of FIG. 1, now engaged to a button and with a lacing tool introduced through a section of the suture and in the process of engaging and end of the suture.

As depicted in FIG. 3, suture 10 has been threaded through two interior apertures 19 of a button 21, which also has two exterior apertures 23. A trap section 20 is defined, between sections 16 and 18, and the barb 24 of the lacing tool 22 is pushed into the lumen of the suture 10 at the fluffed entry point 16. The barb 24 is pushed through the inside of the trap section 20 and guided outward through the fluffed exit point 18. Suture end 12 is then grasped by the barb 24 and drawn through exit point 18 and out through point 16. The result of this operation (not shown) is that tail 12 extends through trap section 20, exiting at point 16, and forming a loop 26 (FIG. 4).

Figure 4:
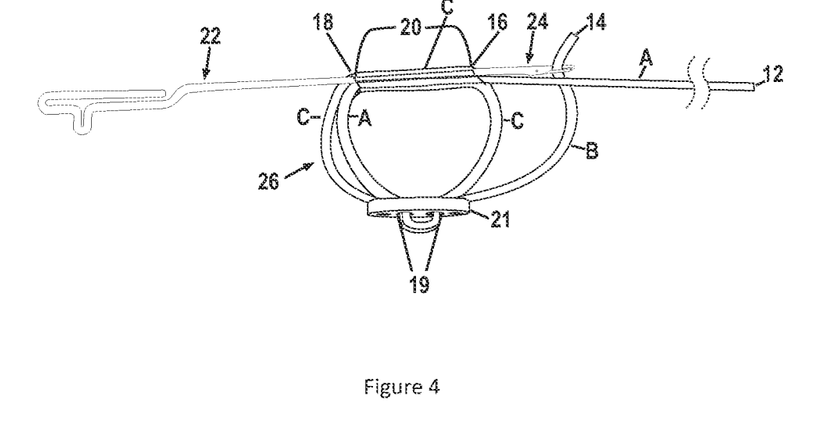
FIG. 4 is an illustration of the elements of FIG. 3, now at a further stage of construction of a suture assembly.
Figure 5:
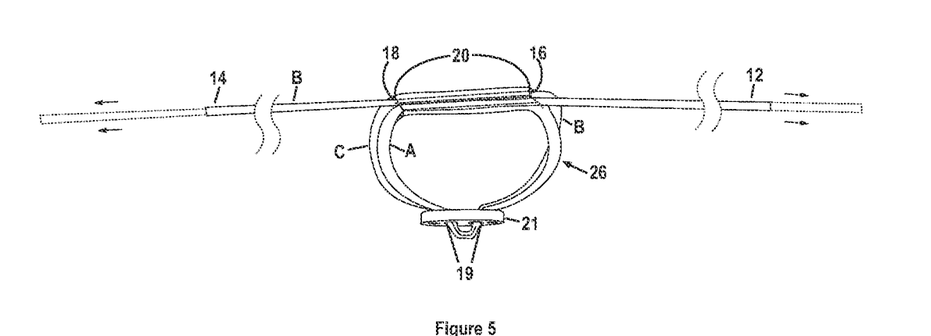
FIG. 5 is an illustration of the elements of FIG. 4, now at a further stage of construction of a suture assembly.

Referring to FIG. 4, second tail 14 is threaded through apertures 19, seized by barb 24 and drawn back through trap section 20, entering through second point 18 and exiting through first point 16. The result is shown in FIG. 5, having a double loop 26, and a tail (12 and 14) extending out of loop 26 in either direction. Trap section 20 is now a double trap 20, having portion A of suture 10 going through double trap 20 from second point 18 to first point 16 and portion B of suture 10 going through double trap 20 in the opposite direction.

Figure 6:
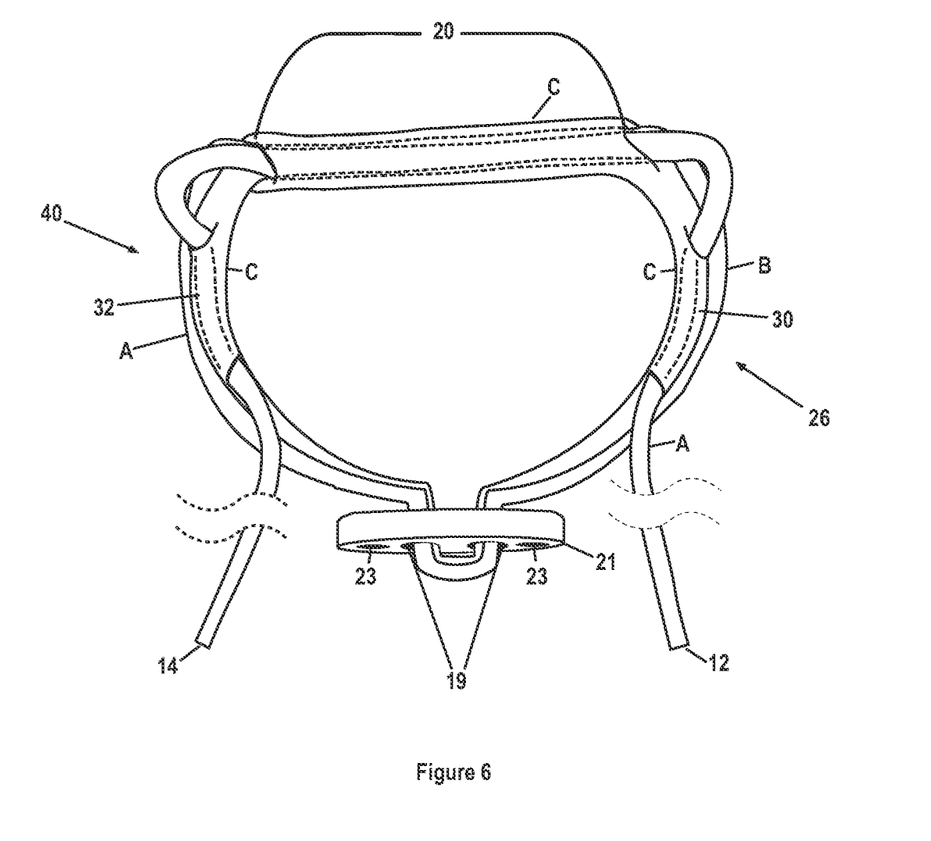
FIG. 6 is an illustration of the elements of FIG. 5, now at a further stage of construction of a suture assembly.
Figure 7:
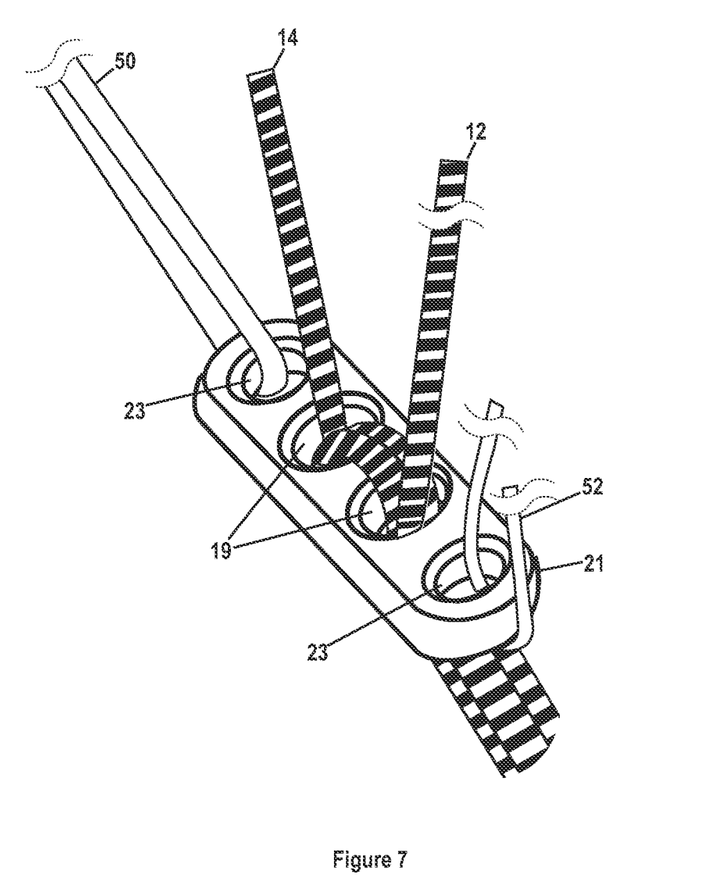
FIG. 7 is an illustration of a top view of a portion of a finished suture assembly according to the present invention.

Referring to FIG. 6, tail 12 is pulled into and then out of a portion of central third C of suture 10, between double trap 20 and the button 21, creating an additional trap 30. A parallel operation is performed, pulling tail 14 into and then out of a portion of central third C of suture 10, between double trap 20 and the button 21, creating yet another trap 32, and a substantially finished suture and button assembly 40. FIG. 7 shows the top portion of assembly 40, with the suture ends 12 and 14 extending through apertures 19, and with positioning and/or connecting tension elements 50 and 52 looped through apertures 23. In a preferred embodiment suture 10 is banded, as shown in FIG. 7.

The three traps 20, 30 and 32 collectively create a greater total amount of resistance to slipping in assembly 40. Slipping can cause an undesirable expansion of the loop 26, after implantation. Accordingly, resistance to slipping, in preventing this undesirable widening, is an important factor in assembly 40 performance. Assembly 40 permits adjustment by cinching of double loop 26, as the assembly 40 is being implanted by a surgeon, and then greatly resists any widening of double loop 26, even during an extensive period of use subsequent to implantation. In an alternative preferred embodiment, tails 12 and 14 are each fed through one of the apertures 19, to provide further resistance to slippage. This design permits 3 mm or less of loop widening through use, after implantation. This is a generally acceptable amount that will not harm a patient. Loop 26 is typically between 12 and 60 mm in circumference.

Non-limiting examples of buttons that can be used with the teachings herein, include the anchor of the XO BUTTON® commercially available by CONMED®/LINVATEC® and suitable buttons disclosed in U.S. Pat. No. 6,533,802 to Bojarski et al., and U.S. Pat. No. 5,306,301 to Graf et al., Thus the buttons used in the teachings herein can be a variety of shapes, non-exclusively including oval, racetrack, circular, square, rectangular, and can have 1, 2, 3, 4, 5, 6, or more apertures for allowing the continuous loop or additional sutures to be threaded through. Apertures can be circular, ovular, square, rectangular, and the like as well. Additionally, the button can include cantilevered arms defining channels, if so desired. Any of the above buttons are suitable in that they can couple to the continuous loop in a manner that an intact button cannot be detached from the loop without opening or breaking the loop.

Buttons are advantageously made from any suitable surgically implantable biocompatible material, non-exclusively including metal, including surgical steel and titanium, or thermoplastics, for example. Alternatively, buttons can be made of a biocompatible thermoplastic as well, for example. In one embodiment the button 21 has a length of between 11 and 12 mm and a width of between 3 and 6 mm. The double trap 20 has a length of between 15 and 18 mm. If loosely pulled the length of double loop 26 from button 21 to the furthest point, in one embodiment is 60 mm. In one embodiment the double loop 26 is stretched beyond 60 mm, from button 21 to furthest point, to set the traps 20, 30 and 32.

Figure 8:
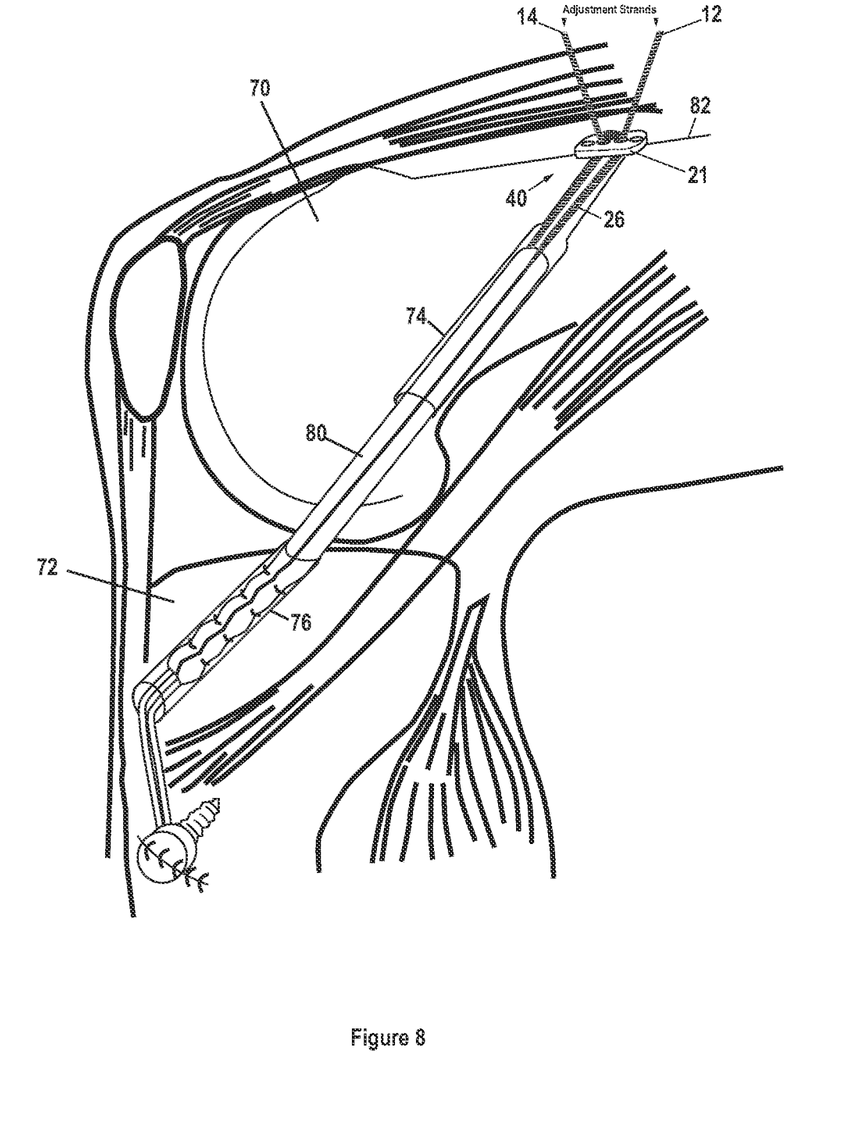
FIG. 8 is an illustration of the suture assembly of FIG. 7 in use in the repair of a knee.

Referring now to FIG. 8, in most typical use, the above described assembly is used in the replacement of the anterior cruciform ligament, binding the femur 70 to the tibia 72. To achieve this end, roughly aligned holes 74 and 76, are drilled through these two bones 70, 72 and a graft ligament 80 is draped over the double loop 26. The button 21 is passed from the tibia 72 through the two aligned holes 74, 76 to emerge at the top of the femur 70, where it is seated on the cortex 82, with the loop 26 extending into the femur hole 74 and the graft ligament 80 extending through the aligned holes 74, 76, from the femur hole 74 to the roughly aligned tibia hole 76. At this point, the suture ends 12, 14 are available to be pulled, on the femur end of the aligned holes 74, 76, and this is done to constrict the double loop and pull the graft ligament into a preferred position for forming attachment to the tunnel walls and binding together the femur 70 and the tibia 72 of the patient. It may also be noted that the loop size may be adjusted prior to surgery, so that a smaller number of sizes can be stocked.

INDUSTRIAL APPLICABILITY

The present invention finds industrial applicability in the manufacture of suture and button assemblies.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A suture assembly, including:
(a) a button having two apertures;
(b) a suture defining a lumen and forming a double loop, formed by a double trap having a first end and a second end, formed in a double trap portion of said suture, opposed to said button, and in which a first portion of said suture is threaded through said lumen of said double trap portion and a second portion of said suture is also threaded through said lumen of said double trap portion, so that two portions of suture are positioned together in said double trap and further wherein said first portion of said suture, after emerging from said double trap, is threaded through said lumen again, thereby forming a second trap, additional to said double trap, and thereby increasing resistance of said double loop to expansion, after it has been tightened, said double loop being threaded through said apertures of said button, said suture having two suture ends that are threaded through said button apertures and accessible on a side of said button opposed to said double loop.

2. The suture assembly of claim 1, wherein said button includes an additional aperture and wherein a thread is engaged with said additional aperture, to permit said button to be pulled through a through-hole.

3. The suture assembly of claim 2, wherein said button includes at least one additional aperture, and wherein a further thread is engaged to said additional aperture and used to position said button.

4. The suture assembly of claim 1, wherein said button is oblong.

5. The suture assembly of claim 1, wherein said suture is banded.

6. The suture assembly of claim 1, wherein said second portion of said suture, after emerging from said first end of said double trap, is threaded into and out of a portion of said lumen on a second side of said double trap, opposed to said first side, thereby forming a third trap, additional to said double trap and said second trap.

7. A method of performing a tendon replacement, of a tendon connecting a first bone and a second bone, in an animal body:
(a) drilling a drill hole sequentially through said two bones;
(b) providing a suture assembly, including:
(i) a button having two apertures;
(ii) a suture defining a lumen and forming a double loop, formed by a double trap having a first end and a second end, formed in a double trap portion of said suture, opposed to said button, and in which a first portion of said suture is threaded through said lumen of said double trap portion and a second portion of said suture is also threaded through said lumen of said double trap portion, so that two portions of suture are positioned together in said double trap and further wherein said first portion of said suture, after emerging from said second end of said double trap, is threaded through said lumen again, thereby increasing resistance of said double loop to expansion, after it has been tightened, said double loop being threaded through said apertures of said button, said suture having two suture ends that are threaded through said button apertures and accessible on a side of said button opposed to said double loop;
(c) draping lengths of tendon tissue over said double loop and passing said button through said drill hole through said first bone and said second bone, and orienting said button to sit on a surface of said second bone and the suture ends extend outwardly through said apertures of said button;
(d) pulling on said suture ends, to constrict said double loop.

8. The method of claim 7, wherein said button includes an additional aperture and wherein a thread is engaged with said additional aperture and said thread is used to pull said button through said drill hole.

9. The method of claim 8, wherein said button includes at least one additional aperture, and wherein a further thread is engaged to said additional aperture and used to position said button.

10. The method of claim 7, wherein said first bone is a tibia and said second bone is a femur.

11. The method of claim 7, wherein said animal body is a human body.

12. The method of claim 7, wherein said button is oblong, and is passed through said drilled hole so that the narrowest dimension of said button faces said drilled hole.

13. The method of claim 7, wherein said suture is banded, to help a health care professional performing said method to assess length.

14. The method of claim 7, wherein said first portion of said suture, after emerging from said second end of said double trap, is threaded through said lumen again by being threaded into and out of a portion of said lumen on a first side of said double trap, thereby forming a second trap, additional to said double trap.

15. The method of claim 14, wherein said second portion of said suture, after emerging from said first end of said double trap, is threaded into and out of a portion of said lumen on a second side of said double trap, opposed to said first side, thereby forming a third trap, additional to said double trap and said second trap.

* * * * *